United States Patent [19]  
Chopra

[11] 4,377,568  
[45] Mar. 22, 1983

[54] PREPARATION OF AQUEOUS ALCOHOLIC DISPERSIONS OF PH SENSITIVE POLYMERS AND PLASTICIZING AGENTS AND A METHOD OF ENTERIC COATING DOSAGE FORMS USING SAME

[75] Inventor: Sham K. Chopra, Montreal, Canada

[73] Assignee: Merck Sharp & Dohme (I.A.) Corp., Kirkland, Canada

[21] Appl. No.: 292,111

[22] Filed: Aug. 12, 1981

[51] Int. Cl.$^3$ .................. A61K 9/58; A61K 9/56; A61K 9/32; A61K 9/30
[52] U.S. Cl. .................................. 424/31; 424/32; 424/33; 424/34; 424/35
[58] Field of Search .............. 424/31, 32, 33, 34, 424/35; 106/181; 524/38; 427/3; 106/196

[56] References Cited

U.S. PATENT DOCUMENTS 3,449,489  6/1969  Gaunt ................................ 424/32
3,935,326  1/1976  Groppenbacher et al. ......... 424/33
4,287,221  9/1981  Tonedachi et al. ................ 424/35

FOREIGN PATENT DOCUMENTS 79103222.0  3/1980  European Pat. Off.

OTHER PUBLICATIONS

Chatfield, H. W. *Varnish Constituents* London, Leonard Hill Limited, 1953, pp. 513, 519, 520, 524 and 526.
Derwent Abstract 39143C/22; 69606A/39; 00460X/01; 20605C/12.

*Primary Examiner*—Delbert R. Phillips
*Assistant Examiner*—F. T. Moezie
*Attorney, Agent, or Firm*—Thomas E. Arther; Mario A. Monaco

[57] ABSTRACT

An enteric coating medium for solid medicinal dosage units is prepared by precipitation of a pH sensitive polymer from an alcoholic solution of such a polymer and a plasticizing agent to produce a suspension of fine particles of a mixture of polymer and plasticizing agent.

10 Claims, No Drawings

PREPARATION OF AQUEOUS ALCOHOLIC DISPERSIONS OF PH SENSITIVE POLYMERS AND PLASTICIZING AGENTS AND A METHOD OF ENTERIC COATING DOSAGE FORMS USING SAME

BACKGROUND OF THE INVENTION

The present invention relates to a method of preparing aqueous dispersions of pH-sensitive pharmaceutically acceptable acid sensitive polymers useful in the efficient enteric coating of solid dosage forms as well as the aqueous dispersions prepared thereby.

BRIEF DESCRIPTION OF THE PRIOR ART

As is well known, certain solid dosage forms are desired to be disintegrated only when they arrive at the intestinal canals upon oral administration and they are imparted with enterosoluble property by providing so-called enteric coating on the surface.

Known enteric coating compositions in the prior art are, for example, prepared by dissolving certain cellulose derivatives such as cellulose acetate phthalate, polyvinylacetate phthalate and the like in a suitable organic solvent to form an organic solution.

These enteric coating compositions in the form of organic solutions have several defects. for example, in the first place, they are undesirable because of the relatively high production cost due to the use of large volumes of organic solvents. Further, there can be problems from the standpoints of safety and environmental pollution since the use of an organic solvent is not free from the danger of fire or explosion in the course of the coating process and emission of the vapor of the organic solvents to the atmosphere causes a difficult problem of environmental pollution. In addition, any traces of the organic solvents remaining in the coating layer on the solid dosage forms are undesirable in consideration of possible toxicity of them. Also concentrated solutions are extremely viscous and thus are difficult to handle.

It is therefore an important problem in the pharmaceutical industry to develop an aqueous enteric coating composition with wide versatility for various kinds of solid dosage forms and free from the above described problems in the prior art composition of organic solution type for enteric coating.

APPLICANT'S DEVELOPMENT

It might be expected that a method of avoiding the toxicity and safety problems would be to employ water or other dispersion medium. However, it is known, that polymers used as enteric film producing substances, are generally water insoluble and thus present difficulties in the preparation of aqueous solutions or dispersions suitable for use in enteric coating of solid dosage forms.

The enteric coating medium used in the process of our invention is an aqueous alcoholic suspension of a pH sensitive enteric coating polymer such as polyvinylacetate phthalate or cellulose acetate phthalate or a mixture thereof in combination with a plasticizing agent such as triethyl citrate (and others) wherein the size of the particles of suspended coating material is less than 1 micron in diameter.

In accordance with the novel process developed by applicant, a solution of plasticizing agent and alcohol is mixed with the selected polymer to form a solution, heating as needed to effect solution. Then there is added to the solution a solution of diluted ammonium hydroxide to produce a suspension containing plasticizing agent and precipitated polymer in which the suspension comprises particles, all of which have a particle size of less than 1 micron in diameter. A part of the polymer is neutralized in the process. The aqueous alcoholic suspension of enteric coating material is particularly advantageous compared to solutions of such polymers in organic solvents since the aqueous suspension is of much lower viscosity than the solvent solution and therefore avoids processing problems caused by highly viscous solutions in the tablet coating equipment.

The coating polymer used in the process of my invention is a polyvinylacetate phthalate polymer and/or a cellulose acetate phthalate polymer. Cellulose acetate phthalate is a reaction product of phthalic anhydride and a partial acetate ester of cellulose. After drying at 105° to 2 hours it contains not less than 19.0% and not more than 23.5% of acetyl groups and not less than 30.0% and not more than 36% of phthalyl(o-carboxybenzoyl) groups calculated in the acid free base. Polyvinylacetate phthalate polymer is a phthalic acid ester of a partially esterified polyvinyl alcohol in which the hydroxyl groups of the vinyl groups are partly esterified by phthalic acid, partly acetylated and partly unreplaced. The polymer is characterized by having a phthalyl content of from 38–70% an acetyl content of from 0.2–12%. A preferred form has a degree of polymerization of about 750, a phthalyl content of about 59% and a acetyl content of about 4.1%.

It is a critical feature of the present invention that the mixture contain a significant amount of a plasticizing agent in association with the coating polymer material to enhance the solubility of the polymer in ethanol. It is desirable to prepare mixtures of polymer and plasticizer wherein the weight of plasticizer present is from 10–40% of the weight of the polymer. Selection of the most desirable plasticizer is dependent on its ability to aid in solubilizing the polymer in ethanol. Examples of plasticizers satisfactory for use in the practice of the present invention are:

Triethyl citrate,
Acetyl triethyl citrate,
Diethyl phthalate,
Dibutyl phthalate,
Dibutyl sebacate,
Dibutyl tartrate,
Dibutyl maleate,
Dibutyl succinate,
Diethyl succinate, with triethyl citrate being preferred. Mixtures of the above compounds are also useful, the mixture of triethyl citrate and diethyl phthalate being preferred.

A further aspect of the present invention is the provision of a solid medicinal oral dosage unit; e.g., a tablet containing at least one solid medicinal agent which comprises a shaped core containing a medicinal agent surrounded by an enteric layer of a pH sensitive polymer selected from cellulose acetate phthalate, polyvinylacetate phthalate and mixtures thereof prepared by deposition from aqueous alcoholic suspensions of small particles of such polymers in which the particle size of such polymers is less than 1 micron in diameter.

Tablets coated with aqueous dispersion of polymer-plasticizer particles of the present invention are deposited with a transparent instead of a translucent or opaque film. Although it is our wish not to be bound by theory, it is believed that the reason for the formation of the desirable, transparent, uniform, and continuous film deposited on the tablets is caused by the present method of precipitating the polymer-plasticizer particles from solution. This method of operation produces an aqueous suspension, containing a small amount of alcohol, of particles of polymer and plasticizer having a diameter of from 0.01 to 1 micron in diameter.

The following examples are provided to illustrate the present invention in greater detail. Enteric coated tablets prepared by the process of my invention can be tested in standard solubility tests to determine the probable disintegration time in the patient's stomach and in the intestinal tract. For the present development, a good enteric coating should not only be soluble at a pH of 7.5 but should also be readily soluble at a pH of 5.5–7.5. In addition it should remain insoluble and prevent tablet disintegration at pH values of 3 or less.

It is also evident that the rate of solubility of an enteric coating material is of prime importance. On the average a tablet will traverse the entire length of the small intestine in a period of 4–5 hours. If a prolonged period is required for the coating to dissolve, the drug will be released only in the lower portion of the intestinal tract where optimum conditions for absorption may not exist. Thus to make the drug available in the duodenum or jejunum, it is highly desirable that the enteric coating be ruptured as soon as possible after leaving the stomach.

Disintegration tests on tablets coated by the aqueous alcoholic dispersion of the present invention showed that they resisted the action of simulated gastric juices (pH 1.5) for at least 3 hours and that they disintegrated in simulated intestinal juice.

PREPARATION OF TABLETS

A batch of 1,000,000 tablets is prepared according to the following formula and procedure.

|  | G. |
|---|---|
| Acetylsalicylic acid crystals | 325,000 |
| Corn starch | 35,000 |
| Lubricant | 10,000 |

The ingredients are well mixed, then slugged to make a 16-mesh granulation. The granulation is then compressed on a tablet machine using 7/16" punches and dies to product 1,000,000 tablets, each weighing 370 mg, and containing 325 mg of acetylsalicylic acid. The tablets are then sub-coated with a water-soluble material using standard techniques known in the art. The batch is then divided into lots of about 30,000 tablets for the application of various enteric coating materials.

TABLET COATING PROCEDURE

The selected number (30,000) of tablets are placed in a perforated rotating coating pan and the aqueous alcoholic dispersion of polymer-plasticizer particles applied as a fine spray along with a stream of warm air to evaporate the liquid as the tablet coat forms.

The procedure is continued until a sufficient thickness is built up to resist penetration by gastric secretion for a period of 2–6 hours.

EXAMPLES—PROCEDURES

Aqueous dispersions of polymers are formed by first mixing a plasticizing agent and ethanol and warming the mixture to 70° C. The amount of plasticizer used is from 10–40% of the weight of polymer or polymer mixture. To the resulting clear solution is then added the polymer and the mixture is stirred until a clear solution is formed. A solution of diluted ammonium hydroxide containing from 4.0 to 6.0 ml of concentrated ammonium hydroxide/200 ml of solution is then added with precipitation of small particles of polymer and plasticizer from solution. This suspension is diluted with water to produce an aqueous dispersion of polymer and plasticizer suitable for use in enteric coating of tablets.

EXAMPLE 1

Following the above procedure a suitable tablet coating aqueous dispersion of cellulose acetate phthalate is prepared using the following formula.

| Ingredients | Quantity | | |
|---|---|---|---|
| Cellulose acetate phthalate | 60 g | 60 g | 60 g |
| Triethyl citrate | 25 g | — | 10 g |
| Diethyl phthalate | — | 30 g | 15 g |
| Alcohol | 60 g | 60 g | 60 g |
| Concentrated ammonium hydroxide (dilutions in 200 ml water) | 4.25 ml | 4.25 ml | 4.25 ml |
| Water qs | 400 g | 400 g | 400 g |

EXAMPLE 2

Following the above procedure, suitable tablet coating aqueous dispersions of a mixture of cellulose acetate phthalate CAP and polyvinylacetate phthalate PVAP are prepared having the following formulae.

| Ingredients | Quantity | | |
|---|---|---|---|
| CAP/PVAP | 48/12 g | 51/9 g | 54/6 g |
| Triethyl citrate | 10 g | 10 g | 15 g |
| Diethyl phthalate | 14 g | 14 g | 9 g |
| Ethyl alcohol | 80 g | 80 g | 80 g |
| Concentrated ammonium hydroxide (dilutions in 200 ml water) | 4.5 ml | 4.5 ml | 4.5 ml |
| Water qs | 400 g | 400 g | 400 g |

EXAMPLE 3

Following the above procedure a suitable tablet coating aqueous dispersion of polyvinylacetate phthalate PVAP is prepared having the following formula:

| Ingredients | Quantity |
|---|---|
| PVAP | 60 g |
| Triethyl citrate | 20 g |
| Ethyl alcohol | 80 g |
| Concentrated ammonium hydroxide (dilutions in 200 ml water) | 4.5 ml |
| Water qs | 400 g |

TABLET TESTING PROCEDURE

Tablets prepared from the aqueous alcoholic suspension illustrated herein above are tested for disintegration time with the following results:

The tablets coated using the methods described in examples 1, 2 and 3 are dried at 45° C. for 18 hours. Disintegration tests are then carried out using the USP XX apparatus at 37° C. and the following test solutions:

1. Simulated gastric fluid test solution USP SGF TS pH 1.5.
2. Simulated intestinal fluid test solution USP SIF TS pH 7.5

The time at which the first of the six tablets developed a rupture in its enteric coating and the time at which the last of the six tablets ruptured was recorded. The results of the disintegration tests are shown in Table I, wherein times reported are the means of these values.

TABLE I

| Example NO. | Average Disintegration time in minutes. | |
|---|---|---|
| | SGF TS pH 1.5 | SIF TS pH 7.5 |
| 1 | over 60 | 12 |
| 2 | over 60 | 10 |
| 3 | over 60 | 8 |

What is claimed is:

1. An aqueous polymer dispersion for providing enteric coating on solid dosage forms which comprises
   (a) an aqueous ethanolic solution as the dispersion medium
   (b) a suspension of fine solid enteric coating particles, said particles comprising a plasticizing agent consisting of triethyl citrate, acetyl triethyl citrate, diethylphthalate, dibutyl phthalate, dibutyl sebacate, dibutyl tartrate, dibutyl maleate, dibutyl succinate or diethyl succinate and a pH sensitive pharmaceutically acceptable acid resistant polymer selected from the group consisting of cellulose acetate phthalate, polyvinyl acetate phthalate, and mixtures thereof wherein the particle size of the solid enteric coating particle is less than 1 micron in diameter, said plasticizing agent being present in an amount by weight of 10–40% of the weight of said acid resistant polymer.

2. An aqueous polymer dispersion for providing enteric coating as claimed in claim 1, wherein the plasticizing agent is triethyl citrate.

3. An aqueous polymer dispersion for providing enteric coating as claimed in claim 1, wherein the plasticizing agent is diethyl phthalate.

4. An aqueous polymer dispersion for providing enteric coating as claimed in claim 1, wherein the plasticizing agent is a mixture of triethyl citrate and diethyl phthalate.

5. An aqueous polymer dispersion for providing enteric coating as claimed in claim 1, wherein the plasticizing agent is dibutyl tartrate.

6. An aqueous polymer dispersion for providing enteric coating as claimed in claim 1, wherein the plasticizing agent is dibutyl sebacate.

7. An aqueous polymer dispersion for providing enteric coating as claimed in claim 1 wherein the pH sensitive acid resistant polymer is cellulose acetate phthalate.

8. An aqueous polymer dispersion for providing enteric coating as claimed in claim 1 wherein the pH sensitive acid resistant polymer is polyvinylacetate phthalate.

9. An aqueous polymer dispersion for providing enteric coating as claimed in claim 1 wherein the pH sensitive acid resistant polymer is a mixture of cellulose acetate phthalate and polyvinylacetate phthalate.

10. A process for the preparation of an aqueous alcoholic suspension of solid particles of a plasticizing agent as defined in claim 1 and an acid resistant pH sensitive polymer said plasticizing agent being present in an amount by weight of 10–40% of the weight of the acid resistant polymer as defined in claim 1 which comprises heating a solution of a plasticizing agent and ethanol with said acid resistant pH sensitive polymer to dissolve said polymer and form an alcoholic solution of plasticizing agent and polymer, contacting said solution with diluted ammonium hydroxide solution to form a suspension comprising a plasticizing agent and precipitated solid particles of an acid resistant pH sensitive polymer, and diluting said suspension with water to form an aqueous alcohol dispersion of said solid particles, said particles having particle diameter of less than 1 micron.

* * * * *